United States Patent
Krig et al.

(10) Patent No.: US 7,194,308 B2
(45) Date of Patent: Mar. 20, 2007

(54) SYSTEM AND METHOD FOR MONITORING OR REPORTING BATTERY STATUS OF IMPLANTABLE MEDICAL DEVICE

(75) Inventors: David B. Krig, Minneapolis, MN (US); Kenneth Tobacman, Cedar, MN (US); Scot Boon, Woodbury, MN (US); Kristofer J. James, Eagan, MN (US); Rajesh Krishan Gandhi, Woodbury, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 429 days.

(21) Appl. No.: 10/706,856

(22) Filed: Nov. 12, 2003

(65) Prior Publication Data

US 2005/0102005 A1 May 12, 2005

(51) Int. Cl.
  A61N 1/36 (2006.01)
  G01N 27/27 (2006.01)
(52) U.S. Cl. .......................... 607/29; 324/433
(58) Field of Classification Search ............ 607/27–29; 320/132; 324/426–433
See application file for complete search history.

(56) References Cited

U.S. PATENT DOCUMENTS

| | | | |
|---|---|---|---|
| 4,259,639 A | 3/1981 | Renirie | 324/430 |
| 4,276,883 A | 7/1981 | McDonald et al. | 128/419 PT |
| 4,290,429 A | 9/1981 | Blaser | 128/419 PT |
| 4,323,075 A | 4/1982 | Langer | 128/419 |
| 4,460,870 A | 7/1984 | Finger | |
| 4,488,555 A | 12/1984 | Imran | 128/419 PT |
| 4,548,209 A | 10/1985 | Wielders et al. | 128/419 |
| 4,556,061 A | 12/1985 | Barreras et al. | 128/419 PT |
| 4,606,350 A | 8/1986 | Frost | 128/419 PG |
| 4,659,994 A | 4/1987 | Poljak | 324/426 |

(Continued)

FOREIGN PATENT DOCUMENTS

EP    0739645 A2    10/1996

(Continued)

OTHER PUBLICATIONS

"WG Wilson Greatbatch Ltd. Reliability Evaluation Report—Model/Part No. CFx", Addendum to RER 96/169: End-of-life (EOL) characteristics for CFx cells, (Jun. 12, 1996), 1 page.

(Continued)

*Primary Examiner*—Robert E. Pezzuto
*Assistant Examiner*—Jessica L. Reidel
(74) *Attorney, Agent, or Firm*—Schwegman, Lundberg, Woessner & Kluth, P.A.

(57) ABSTRACT

A system and method monitors or reports the battery status of an implantable medical device to a user. The battery terminal voltage and charge delivered are measured. Before the battery terminal voltage falls below an Elective Replacement Indicator (ERI) threshold voltage, a charge-delivered indication of battery status is provided to a user. Thereafter, a battery terminal voltage indication of battery status is provided to a user. The Elective Replacement Indicator (ERI) and End of Life (EOL) threshold voltages are each functions of delivered battery current. A fault current detection is also provided to a user. A device temperature sensor discounts the battery voltage reading when the device is too cold.

44 Claims, 5 Drawing Sheets

U.S. PATENT DOCUMENTS

| | | | |
|---|---|---|---|
| 4,709,202 A | 11/1987 | Koenck et al. ............... 320/43 |
| 4,712,179 A | 12/1987 | Heimer ...................... 364/417 |
| 4,947,124 A | 8/1990 | Hauser |
| 4,952,864 A | 8/1990 | Pless et al. ................. 323/299 |
| 5,137,020 A | 8/1992 | Wayne et al. .......... 128/419 PS |
| 5,344,431 A | 9/1994 | Merritt et al. ................ 607/29 |
| 5,369,364 A | 11/1994 | Renirie et al. ............... 324/430 |
| 5,370,668 A | 12/1994 | Shelton et al. ................ 607/29 |
| 5,372,605 A | 12/1994 | Adams et al. |
| 5,391,193 A | 2/1995 | Thompson ................... 607/29 |
| 5,402,070 A | 3/1995 | Shelton et al. .............. 324/433 |
| 5,411,537 A | 5/1995 | Munshi et al. |
| 5,458,624 A | 10/1995 | Renirie et al. ................ 607/29 |
| 5,483,165 A | 1/1996 | Cameron et al. ........... 324/427 |
| 5,496,353 A | 3/1996 | Grandjean et al. ............ 607/29 |
| 5,527,630 A | 6/1996 | Nagata et al. ................. 429/7 |
| 5,540,724 A | 7/1996 | Cox ............................. 607/8 |
| 5,562,595 A | 10/1996 | Neisz .......................... 600/16 |
| 5,591,213 A | 1/1997 | Morgan ......................... 607/5 |
| 5,620,474 A | 4/1997 | Koopman |
| 5,675,258 A | 10/1997 | Kadouchi et al. ........... 324/433 |
| 5,690,685 A | 11/1997 | Kroll et al. .................... 607/5 |
| 5,700,280 A | 12/1997 | Silvian .......................... 607/5 |
| 5,713,936 A | 2/1998 | Staub .......................... 607/29 |
| 5,721,482 A | 2/1998 | Benvegar et al. ............. 320/43 |
| 5,741,307 A | 4/1998 | Kroll ............................. 607/5 |
| 5,769,873 A | 6/1998 | Zadech ........................ 607/29 |
| 5,800,472 A | 9/1998 | Mann ........................... 607/29 |
| 5,836,973 A | 11/1998 | Kroll ............................. 607/5 |
| 5,869,970 A | 2/1999 | Palm et al. ................... 324/433 |
| 5,896,423 A | 4/1999 | Okamoto .................... 375/345 |
| 5,897,576 A | 4/1999 | Olson et al. .................... 607/5 |
| 5,904,705 A | 5/1999 | Kroll et al. .................... 607/5 |
| 5,925,068 A * | 7/1999 | Kroll ............................ 607/29 |
| 5,929,601 A | 7/1999 | Kaib et al. ................... 320/113 |
| 5,959,371 A | 9/1999 | Dooley et al. .............. 307/130 |
| 5,998,968 A | 12/1999 | Pittman et al. |
| 6,016,488 A | 1/2000 | Bosworth et al. ............... 707/4 |
| 6,018,227 A | 1/2000 | Kumar et al. ................ 320/106 |
| 6,045,941 A | 4/2000 | Milewits ...................... 429/91 |
| 6,108,579 A | 8/2000 | Snell et al. .................... 607/29 |
| 6,114,838 A | 9/2000 | Brink et al. ................. 320/136 |
| 6,148,235 A | 11/2000 | Kuiper ......................... 607/29 |
| 6,154,675 A | 11/2000 | Juran et al. .................... 607/29 |
| 6,166,524 A | 12/2000 | Takeuchi et al. |
| 6,167,309 A | 12/2000 | Lyden .......................... 607/29 |
| 6,169,387 B1 | 1/2001 | Kaib ............................ 320/132 |
| 6,185,461 B1 | 2/2001 | Er ................................ 607/27 |
| 6,198,253 B1 | 3/2001 | Kurle et al. ................. 320/132 |
| 6,274,265 B1 | 8/2001 | Kraska et al. ................ 429/90 |
| 6,281,683 B1 | 8/2001 | Podrazhansky et al. |
| 6,307,379 B2 | 10/2001 | Podrazhansky et al. |
| 6,313,609 B1 | 11/2001 | Brink .......................... 320/132 |
| 6,366,056 B1 | 4/2002 | Podrazhansky et al. |
| 6,366,809 B1 | 4/2002 | Olson et al. .................... 607/5 |
| 6,377,850 B1 | 4/2002 | Takeuchi et al. |
| 6,400,988 B1 | 6/2002 | Gurewitsch .................. 607/29 |
| 6,426,628 B1 | 7/2002 | Palm et al. .................. 324/427 |
| 6,472,847 B2 | 10/2002 | Lundberg .................... 320/132 |
| 6,490,486 B1 | 12/2002 | Bradley ........................ 607/28 |
| 6,503,646 B1 | 1/2003 | Ghantous et al. |
| 6,563,318 B2 | 5/2003 | Kawakami et al. |
| 6,584,355 B2 | 6/2003 | Stessman ..................... 607/29 |
| 6,671,552 B2 | 12/2003 | Merritt et al. ................ 607/29 |
| 6,696,842 B2 | 2/2004 | Traub |
| 6,744,152 B2 | 6/2004 | Kroll ........................... 307/66 |
| 6,760,625 B1 | 7/2004 | Kroll ........................... 607/29 |
| 6,768,288 B2 * | 7/2004 | Rosenquist et al. ......... 320/132 |
| 6,861,842 B2 | 3/2005 | Baeuerlein et al. |
| 6,885,894 B2 | 4/2005 | Stessman |
| 6,930,468 B2 | 8/2005 | Syracuse et al. |
| 6,940,255 B2 * | 9/2005 | Loch ........................... 320/132 |
| 2003/0065366 A1 | 4/2003 | Merritt et al. ................ 607/27 |
| 2003/0176897 A1 | 9/2003 | Stessman ..................... 607/27 |
| 2003/0204219 A1 * | 10/2003 | Gielen ......................... 607/45 |
| 2004/0039424 A1 | 2/2004 | Merritt et al. ................ 607/29 |
| 2004/0162592 A1 | 8/2004 | Betzold et al. ............... 607/27 |
| 2005/0007073 A1 | 1/2005 | James et al. |
| 2005/0088145 A1 | 4/2005 | Loch |
| 2005/0143782 A1 | 6/2005 | Stessman |

FOREIGN PATENT DOCUMENTS

| | | |
|---|---|---|
| EP | 0770411 A2 | 5/1997 |
| EP | 0642369 B1 | 8/1998 |
| EP | 138297 | 1/2004 |
| WO | WO-94/02202 A1 | 2/1994 |
| WO | WO-02/19448 A1 | 3/2002 |
| WO | WO-02/089904 A2 | 11/2002 |
| WO | WO-2004/062009 A2 | 7/2004 |

OTHER PUBLICATIONS

"WG Wilson Greatbatch Ltd. Reliability Evaluation Reports—Model/Part No.: 9424", Subject: Model 9424 Li/CFx cell fuel gauge, (Aug. 7, 1998),3 pages.

James, K. J., et al., "Indicator of Remaining Energy in Storage Cell of Implantable Medical Device", U.S. Appl. No. 10/618,095, filed Jul. 11, 2003, 25 pages.

Linden, David, "Handbook of Batteries", pp. 2.1, 2.5-6, 2.25, 14.1 and 14.68.

Loch, R., "Battery Charge Indicator Such as for an Implantable Medical Device", U.S. Appl. No. 10/692,315, filed Oct. 23, 2003, 33 pages.

Parsonnet, V., "Cardiac pacing and pacemakers VII. Power sources for implantable pacemakers. Part I.", *American Heart Journal*, 94 (4), (Oct. 1977),pp.517-528.

Takeuchi, E. S., et al., "Lithium/Silver Vanadium Oxide Batteries for Implantable Defibrillators", *PACE*, 11, (Nov. 1988),2035-2039.

* cited by examiner

SYSTEM AND METHOD FOR MONITORING OR REPORTING BATTERY STATUS OF IMPLANTABLE MEDICAL DEVICE

CROSS-REFERENCE TO RELATED PATENT APPLICATIONS

This patent application is related to Stessman, U.S. Pat. No. 6,584,355 entitled "SYSTEM AND METHOD FOR MEASURING BATTERY CURRENT," which is assigned to Cardiac Pacemakers, Inc., and which is incorporated by reference herein in its entirety, including its disclosure of tracking charge depletion from a battery.

This patent application is also related to Stessman et al. U.S. patent application Ser. No. 10/395,983, filed on Mar. 25, 2003, now issued as U.S. Pat. No. 6,885,894, entitled "SYSTEM AND METHOD FOR MEASURING BATTERY CURRENT," which is assigned to Cardiac Pacemakers, Inc., and which is incorporated by reference herein in its entirety.

This patent application is also related to James et al. U.S. patent application Ser. No. 10/618,095, filed on Jul. 11 2003, entitled "INDICATOR OF REMAINING ENERGY IN STORAGE CELL OF IMPLANTABLE MEDICAL DEVICE," which is assigned to Cardiac Pacemakers, Inc., and which is incorporated by reference herein in its entirety.

This patent application is also related to Loch U.S. patent application Ser. No. 10/692,315, filed Oct. 23, 2003, now issued as U.S. Pat. No. 6,940,255, entitled "BATTERY CHARGE INDICATOR SUCH AS FOR AN IMPLANTABLE MEDICAL DEVICE," which is assigned to Cardiac Pacemakers, Inc., and which is incorporated by reference herein in its entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

This patent application pertains generally to batteries, and more particularly, but not by way of limitation, to a system and method for monitoring or reporting battery status of an implantable medical device.

BACKGROUND

Implantable medical devices include, among other things, cardiac rhythm management (CRM) devices such as pacers, cardioverters, defibrillators, cardiac resynchronization therapy (CRT) devices, as well as combination devices that provide more than one of these therapy modalities to a subject. Such implantable devices are typically powered by a battery. When the battery's useful life has expired, the implanted device is typically explanted and replaced. Therefore, it is often useful to know how much battery energy has been used and/or how much battery energy remains.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

Figure 1:
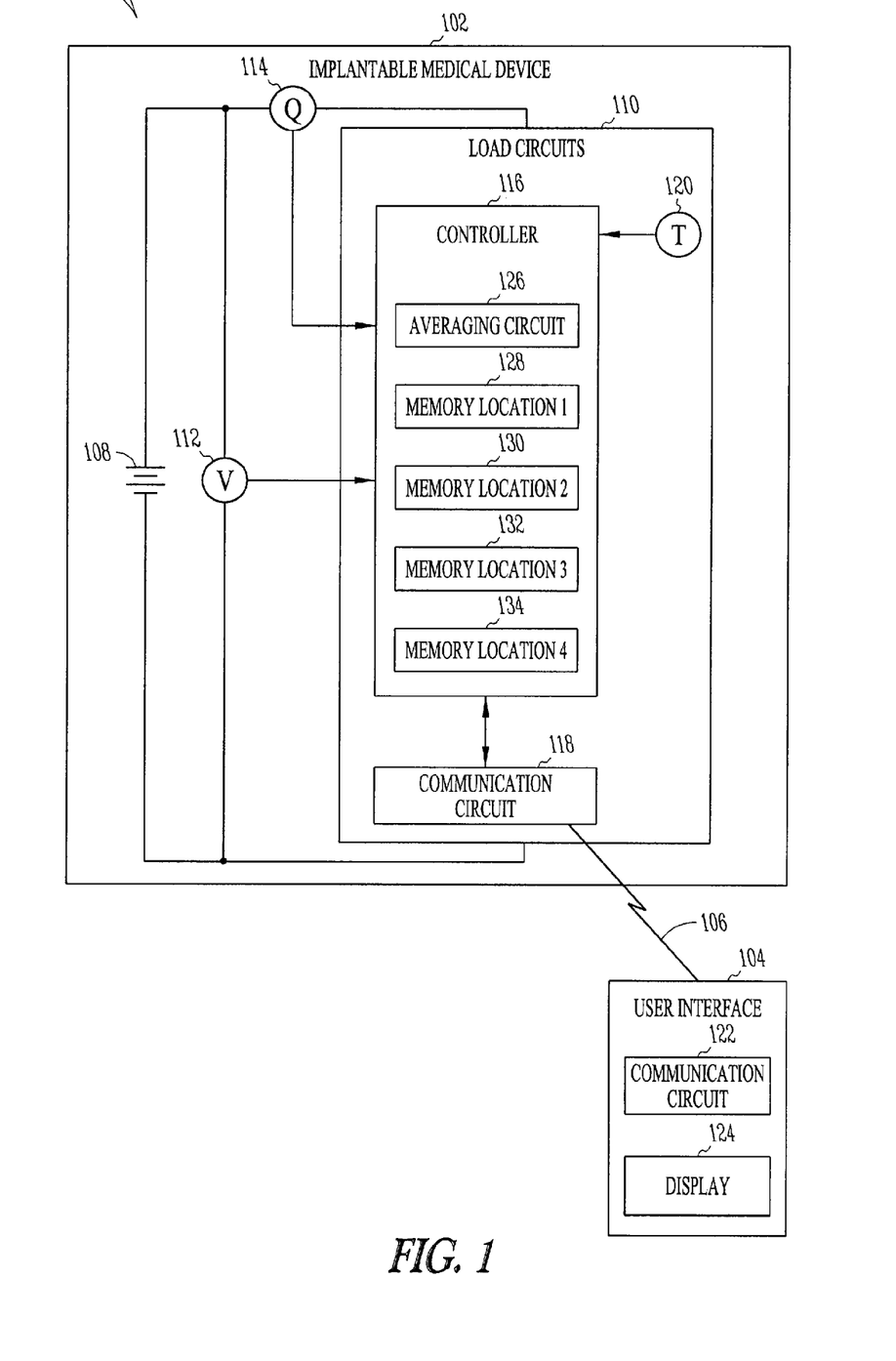
FIG. 1 is a schematic/block diagram illustrating generally one example of a system 100 that includes an implantable medical device and an external user interface device.

FIG. 1 is a schematic/block diagram illustrating generally one example of a system 100. In this example, the system 100 includes an implantable medical device 102, such as a cardiac rhythm management device, for example. In this example, the system 100 also includes an external programmer or other user interface device 104. The user interface 104 is operatively communicatively coupled to the device 102, such as by using a wireless or other communications link 106.

In the example of FIG. 1, the device 102 includes a battery 108. The battery 108 provides electrical energy to load circuits 110 of the device 102. It is useful to know how much of the stored energy of the battery 108 has been used (or, alternatively, how much usable energy remains in the battery 108). Among other things, such battery status information helps a physician or other user plan for when the implantable medical device 102 should be explanted from a subject and replaced by another device having a fresh battery.

One technique for determining the battery status measures the battery terminal voltage. The measured battery terminal voltage is used directly to provide a battery status indicator. However, such a technique may be ineffective for certain battery chemistries (e.g., a Lithium Carbon Monofluoride "LiCFx" battery) that manifest a relatively flat battery terminal voltage from the beginning and over most of the battery's useful life. Another technique for determining battery status, such as for an implantable defibrillator, measures an elapsed time for charging a defibrillation capacitor to infer the battery status. Such an elapsed time increases along with the internal battery impedance, which increases as the battery is depleted of charge. However, such a technique is also ineffective for certain battery chemistries (e.g., a LiCFx battery, which has a very low internal battery resistance that does not change appreciably during a time from the beginning and over most of the battery's useful life). By contrast, the system 100 of FIG. 1 provides an alternative way to provide battery status information throughout the battery's useful life, even for a LiCFx battery, or for other batteries having similar battery terminal voltage and/or battery impedance characteristics.

In the example of FIG. 1, the device 102 includes a battery terminal voltage measurement circuit 112, a battery charge measurement circuit 114, a controller circuit 116, a communication circuit 118, and a temperature sensor circuit 120. In this example, the battery terminal voltage measurement circuit 112 is connected in parallel with the battery 108, i.e., across the battery terminals of the battery 108. The battery charge measurement circuit 114 is connected in series with the battery 108, i.e., between the battery 108 and the load circuits 110. The controller 116 is coupled to the battery terminal voltage measurement circuit 112, the battery charge measurement circuit 114, and the temperature sensor circuit 120 to respectively receive a battery terminal voltage measurement, a battery current measurement, and a device 102 temperature measurement. In one example, the controller 116 further includes averaging circuit 126 and memory location locations 128–134. In one example, the battery charge measurement circuit 114 is a battery charge and current measurement circuit, such as described in the above-incorporated Stessman U.S. Pat. No. 6,584,355. In the example of FIG. 1, the external user interface 104 includes a communication circuit 122 and a display 124.

Figure 2:
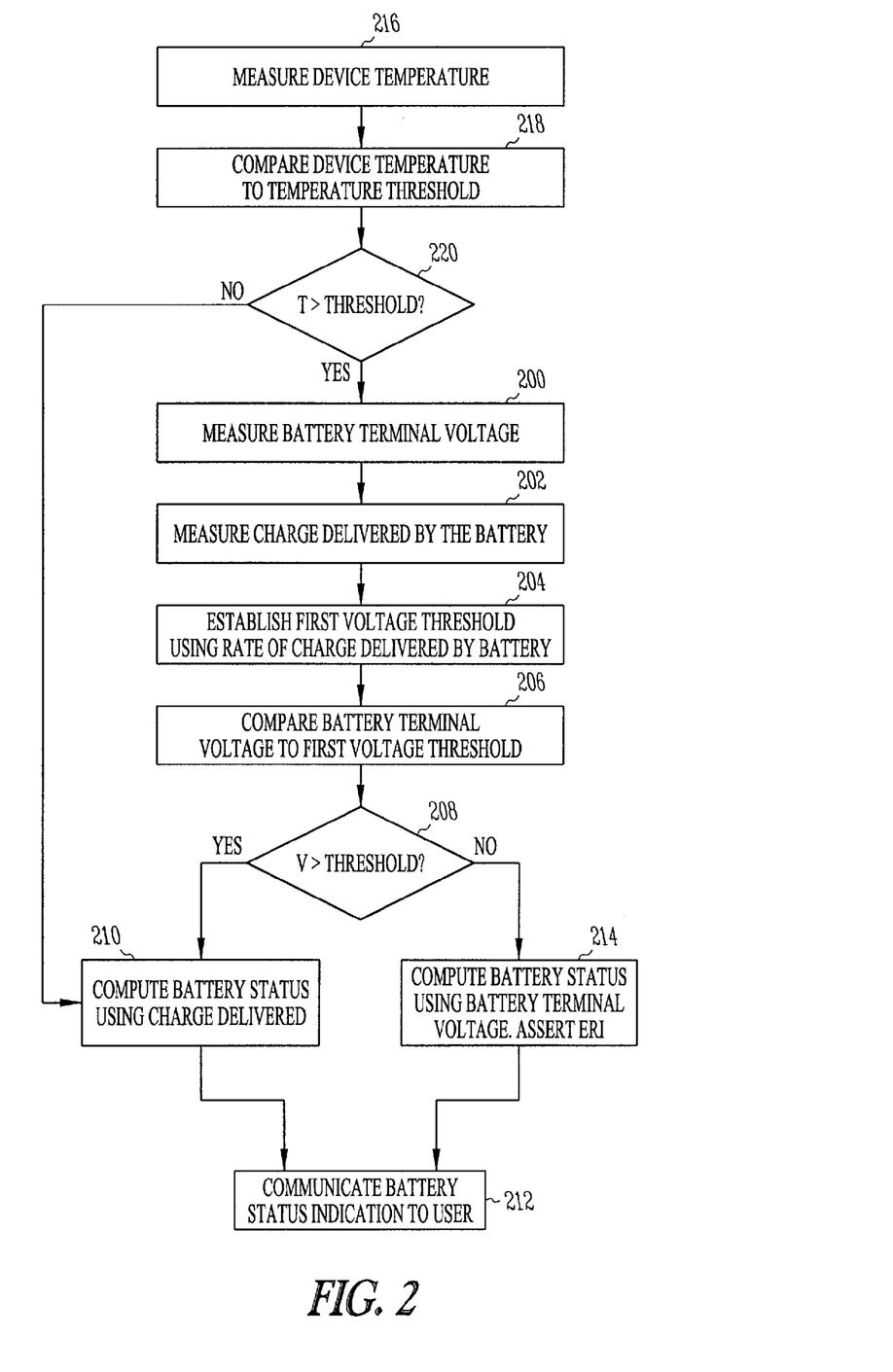
FIG. 2 is a flow chart illustrating generally one example of a technique of providing battery status information.

FIG. 2 is a flow chart illustrating generally one example of a technique of providing battery status information, such as by using the system 100 of FIG. 1. At 200, a battery terminal voltage is measured, such as by using the battery terminal voltage measurement circuit 112. At 202, a charge delivered by the battery 108 is measured, such as by using the battery charge and battery current measurement circuit described in the above-incorporated Stessman U.S. Pat. No. 6,584,355. At 204, a first voltage threshold is established using a rate of charge delivered by the battery. Therefore, the first voltage threshold is a function of the battery current. The exact function may vary, such as to obtain a desired degree of accuracy in the appropriate first voltage threshold over a range of battery current drains. In one illustrative example of the particular function (but not by way of limitation) for a particular battery chemistry and design, if the measured battery current exceeds a particular current threshold value (e.g., 45 microamperes), then a first voltage threshold value of 2.81 Volts is established, otherwise a different first voltage threshold value of 2.78 Volts is established (additional current threshold values and corresponding first voltage thresholds could also be used). In one example, an average of the measured battery current (e.g., over an averaging time period of about 1 week) is used for comparing against the current threshold. In one example, this comparison of average measured battery current to the current threshold is performed once each such averaging time period.

At 206, a measured battery terminal voltage is compared to the first voltage threshold that was established at 204. At 208, if the measured battery terminal voltage exceeds the first voltage threshold, then at 210 a battery charge status indicator is computed using the measurement of how much charge has been previously delivered by the battery 108. At 212, this charge-delivered based battery status indicator is then communicated to the user, such as over communication link 106 for display to the user on the display 124 of the user interface 104. In one example, this communication takes place the next time that the device 102 is interrogated by the user interface 104, however, this communication could alternatively be initiated by the device 102 rather than the user interface 104.

At 208, if the measured battery terminal voltage does not exceed the first voltage threshold, then an elective replacement indicator ("ERI") flag is set at 214. Assertion of the ERI flag corresponds to a predicted subsequent time period (e.g., 6 months) before battery expiration is expected. In this example, assertion of the ERI flag also triggers a switch from a charge-delivered based battery status indicator to subsequent use of a battery terminal voltage based battery status indicator. After ERI is asserted, the battery terminal voltage based battery status indicator (e.g., "ERI asserted") is communicated at 212 to the user. In one example, this communication takes place the next time that the device 102 is interrogated by the user interface 104, however, this communication could alternatively be initiated by the device 102 rather than the user interface 104.

In the method discussed above with respect to FIG. 2, operation has been described, for conceptual clarity, using a single comparison of the battery voltage to the first voltage threshold to determine whether to assert ERI. However, in a further example, ERI is only asserted if three consecutive such comparisons indicate a battery voltage that has fallen below the first voltage threshold. Each such comparison of the battery voltage to the first voltage is made about once per day (e.g., every 21 hours). In one example, the battery voltage reading is an average reading over the same time period of about once per day (e.g., 21 hours).

Moreover, in the method illustrated in FIG. 2, storage of the battery at a cold temperature (e.g., if the implantable device 102 is left in an automobile trunk in a cold climate) may cause the battery terminal voltage to drop. However, such temporary temperature-related drops in battery terminal voltage are not indicative of the state of the battery's charge. The battery terminal voltage will recover when the device 102 is implanted into a patient and the device 102 is warmed to the patient's body temperature. Accordingly, in one example, at 216, the device 102 includes a temperature sensor 120 to measure the temperature of the device. At 218, the temperature is compared to a temperature threshold (e.g., about 10 degrees Celsius, or some other suitable temperature threshold). At 220, if the device 102 temperature falls below the temperature threshold, then the battery voltage measurement is discounted (e.g., inhibited or ignored), at least for the purposes of making a comparison to a voltage threshold for asserting ERI.

Figure 3:
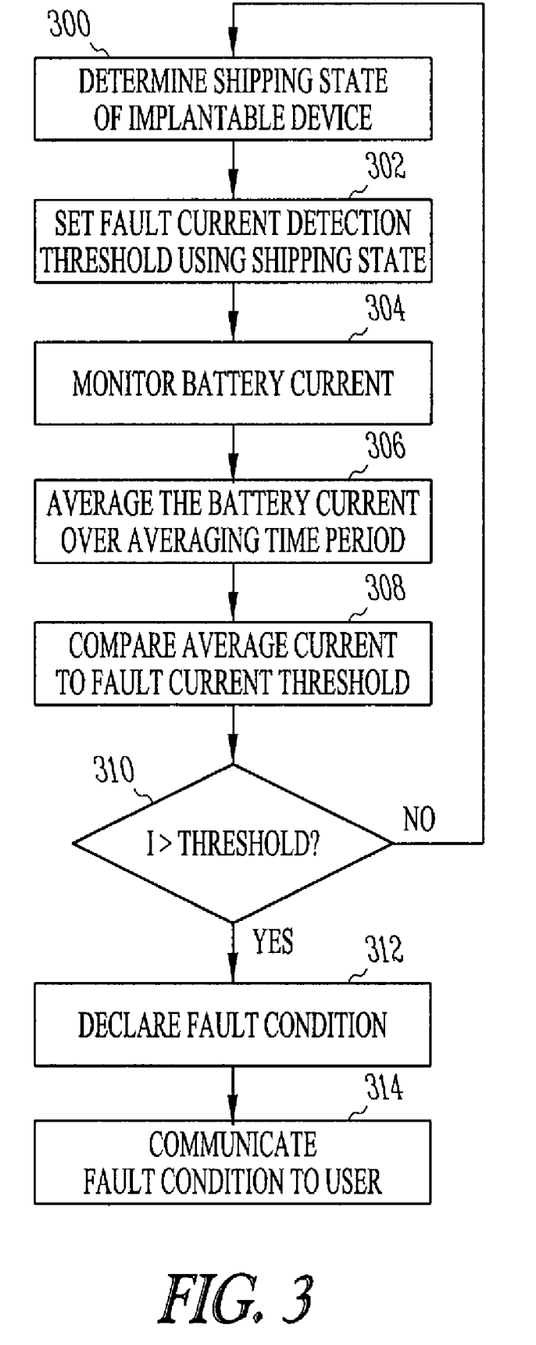
FIG. 3 is a flow chart illustrating generally a fault current detection process.

FIG. 3 is a flow chart illustrating generally a fault current detection process. In one example, the fault current detection process runs concurrent with 202 or one of the other acts illustrated in FIG. 2. At 300, a shipping state of the device 102 is determined, such as by reading a memory storage location (e.g., memory storage location 130) that includes such information. The shipping state of the device 102 indicates whether the device is in a shipping mode, which is the state of the device 102 when it leaves the manufacturing facility. After the device 102 has been implanted in a patient, it is programmed out of the shipping mode by the user. At 302, a fault current detection threshold is set, such as by using the shipping state information. In one illustrative example, if the shipping state indicates that the device 102 is in a shipping mode, then the fault current detection threshold is set to 24 microamperes (or other suitable value for detecting an abnormally elevated current in the shipping mode). In this example, if the shipping state indicates that the device 102 has been implanted in a patient, then the fault current detection threshold is set to 200 microamperes (or other suitable value for detecting an abnormally elevated current in the implanted mode).

At 304, a battery current is monitored, such as by using the battery charge measurement circuit 114, as discussed above. At 306, the monitored battery current is averaged, such as by the averaging circuit 126 of controller 116, over a suitable averaging time period (for example, about 1 day, such as about 21 hours) for performing the fault current detection. This averaging time period may be different than the averaging time period discussed above for establishing the first voltage threshold using the monitored battery current. At 308, the average current is compared (e.g., once per averaging period) to the fault current detection threshold that was set at 302. At 310, if the average current exceeds the fault current detection threshold, ten a fault current detection condition is declared at 312, and the assertion of the fault current detection condition is communicated to the user at 314. Otherwise, if at 310 the average current does not exceed the fault current detection threshold, then process flow returns to 300.

In one example, the average current must exceed the fault current detection threshold for two consecutive averaging time periods for the fault condition to be declared at 312.

Figure 4:
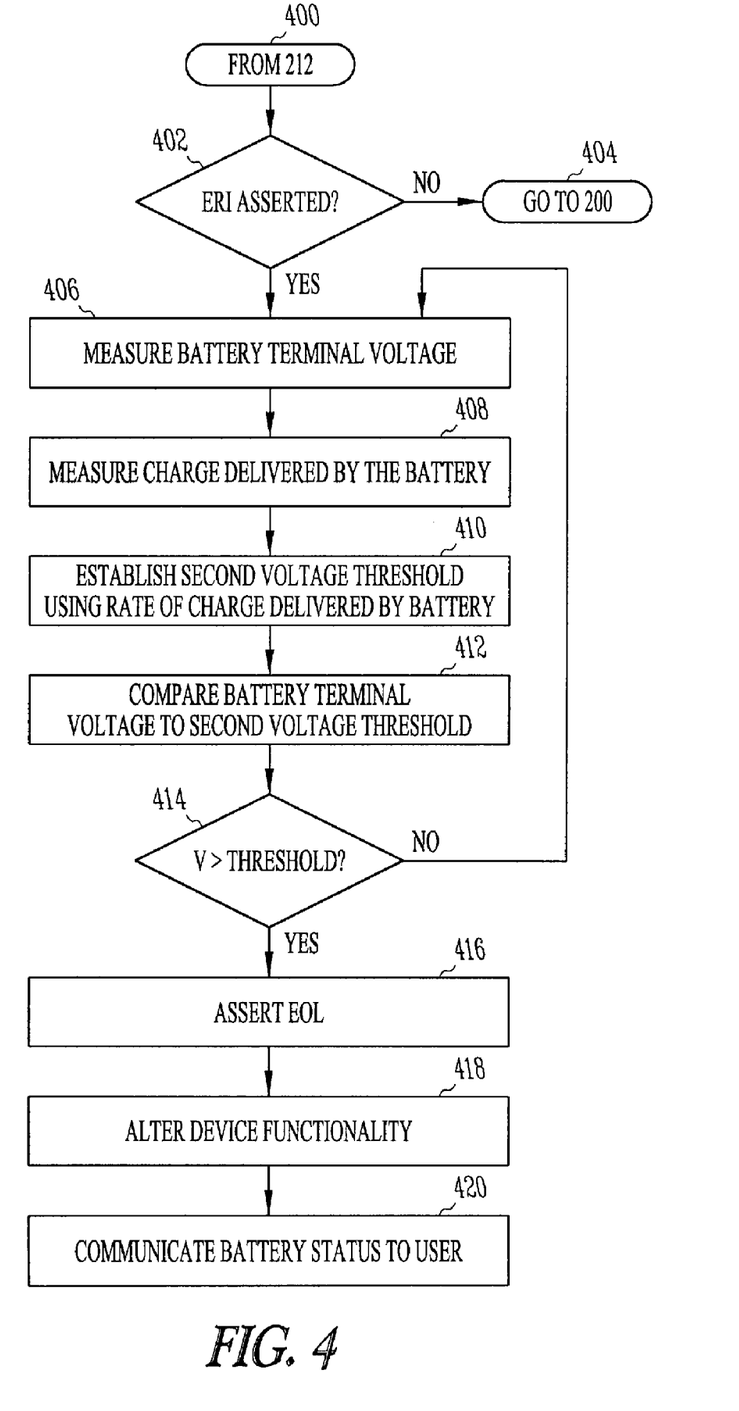
FIG. 4 is a flow chart illustrating generally an example of a further method including acts in addition to those illustrated in FIG. 2.

FIG. 4 is a flow chart illustrating generally an example of a further method including acts in addition to those illustrated in FIG. 2. In the example of FIG. 4, at 400, process flow continues from 212 of FIG. 2. At 402, if ERI has not yet been asserted, then at 404 process flow continues to 200 of FIG. 2. At 402, if ERI has been asserted, then at 406 a battery terminal voltage is measured, such as by using the battery terminal voltage measurement circuit 112. At 408, a charge delivered by the battery 108 is measured, such as by using the battery charge and battery current measurement circuit described in the above-incorporated Stessman U.S. Pat. No. 6,584,355. At 410, a second voltage threshold is established using a rate of charge delivered by the battery. The second voltage threshold is a function of the battery current; the exact function may vary, such as to obtain a desired degree of accuracy in the appropriate threshold voltage over a range of battery current drains. In one illustrative example, if the battery current exceeds a particular current threshold value (e.g., 45 microamperes), then a second voltage threshold value of 2.52 Volts is used, otherwise a different second voltage threshold value of 2.50 Volts is used. In one example, an average of the measured battery current (e.g., over an averaging time period of about 1 week) is used for comparing against the current threshold. In one example, this comparison is performed once each such averaging time period.

At 412, a measured battery terminal voltage is compared to the second voltage threshold that was established at 410. At 414, if the measured battery terminal voltage exceeds the second voltage threshold, then process flow returns to 406, otherwise process flow continues to 416, where an end of life ("EOL") flag is set at 416. Assertion of the EOL flag corresponds to a predicted subsequent time period (e.g., 3 months) before battery expiration is expected. In this example, assertion of the EOL flag also optionally alters device 102 functionality at 418. In one such example, assertion of the EOL flag results in turning off one or more of: diagnostic features, rate responsive pacing, atrial pacing, and/or bi-ventricular pacing. After EOL is asserted, the battery terminal voltage based battery status indicator (e.g., "EOL asserted") is communicated at 420 to the user. In one example, this communication takes place the next time that the device 102 is interrogated by the user interface 104, however, this communication could alternatively be initiated by the device 102 rather than the user interface 104. In one example, the battery voltage measurement is discounted (at least for the purposes of making a comparison to a voltage threshold for asserting ERI) if the temperature of the device 102 falls below a threshold value, as discussed above with respect to FIG. 2.

In the method discussed above with respect to FIG. 4, operation has been described, for conceptual clarity, using a single comparison of the battery voltage to the second voltage threshold to determine whether to assert EOL. However, in a further example, EOL is only asserted if three consecutive such comparisons indicate a battery voltage that has fallen below the second voltage threshold. Each such comparison of the battery voltage to the second voltage is made about once per day (e.g., every 21 hours). In one example, the battery voltage reading is an average reading over the same time period of about once per day (e.g., 21 hours). Moreover, if the device 102 is in a pre-ERI state, and receives three consecutive battery voltage comparisons below the second voltage threshold, then both ERI and EOL are asserted; the device 102 need not spend time in the intermediate ERI state.

Figure 5:
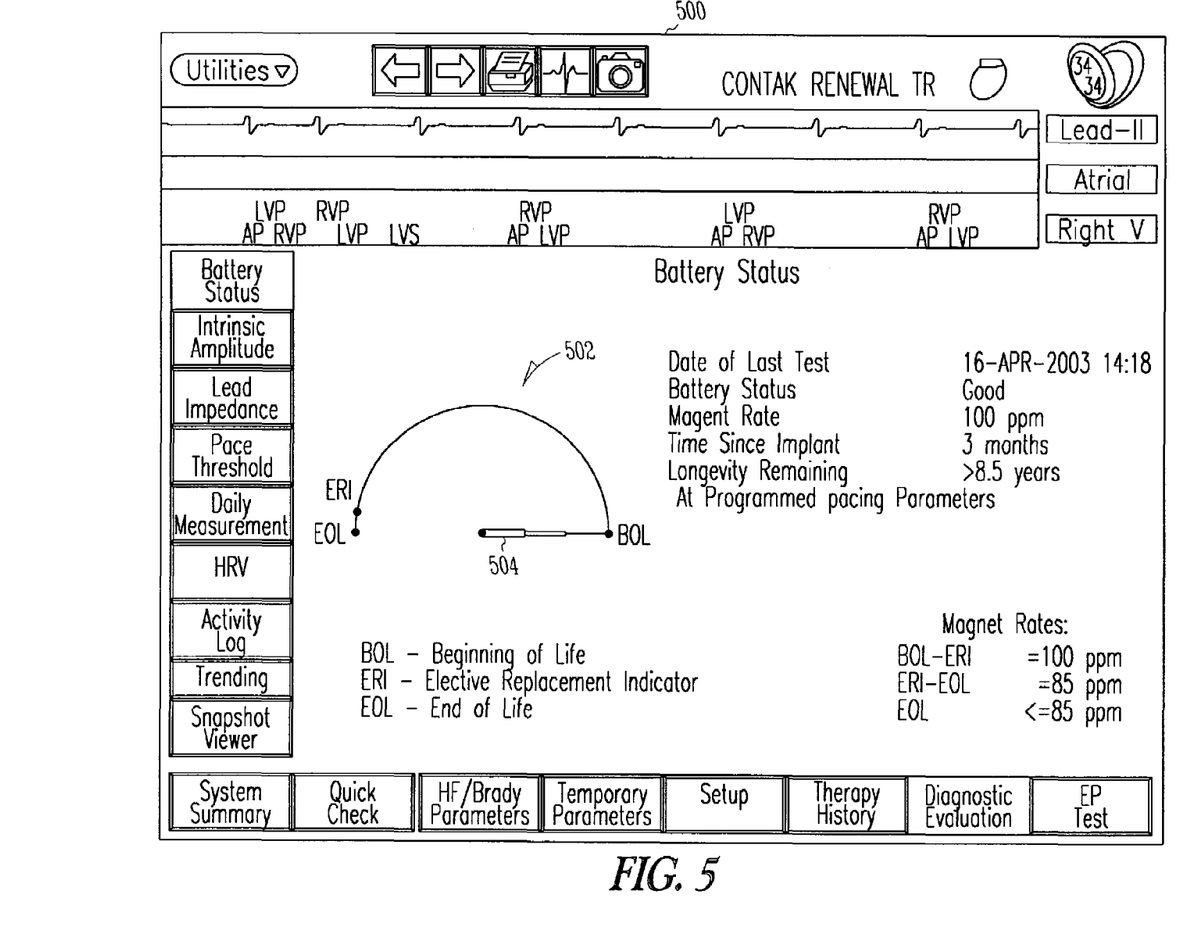
FIG. 5 is a user interface display screenshot of a battery status screen 500 displayed on the display 124 of the user interface 104.

FIG. 5 is a user interface display screenshot of a battery status screen 500 displayed on the display 124 of the user interface 104. In this example, the battery status screen 500 includes a "gas gauge" type of meter 502 displaying a needle 504 that moves from a beginning of life ("BOL") position to an ERI position, and then to an EOL position as charge is depleted from the battery 108. During the time between BOL and ERI, the "gas gauge" type of meter indication of battery charge status is derived from measuring charge depleted from the battery, as discussed above. Upon detection of ERI and thereafter, the "gas gauge" type of meter indication of battery charge status is derived from the measured battery terminal voltage, as discussed above. In this example, the battery status screen also includes information about one or more of: the date of the last battery test, a qualitative indicator of battery status (e.g., "good," "bad," etc.), a magnet rate (i.e., a fixed rate that will result from placing a magnet near the device 102, where the value of the fixed rate will be different depending on the battery status, e.g., 100 ppm between BOL and ERI, 85 ppm between ERI and EOL, and less than or equal to 85 ppm after EOL), a time since the device 102 was implanted, and/or a longevity remaining at the programmed pacing parameters (e.g., pulsewidth, amplitude, and pacing mode).

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. A method comprising:
    measuring a battery terminal voltage of a battery of an implantable medical device;
    measuring a charge delivered by the battery during a first time period after the device has been implanted and before the battery terminal voltage falls below a first voltage threshold, wherein the first voltage threshold is a function of a measured rate at which the charge is delivered by the battery;
    calculating an available or depleted battery charge using the measured charge delivered by the battery during the first time period;
    communicating to a user an indication of the available or depleted battery charge; and
    communicating to the user an indication of whether the battery terminal voltage has fallen below the first voltage threshold.

2. The method of claim 1, in which the measuring the charge delivered by the battery comprises measuring a current delivered by the battery.

3. The method of claim 2, further comprising:
    comparing the measured current delivered by the battery to a current threshold;
    declaring a current fault if the measured current delivered by the battery exceeds the current threshold; and
    communicating to the user an indication of whether the current fault has been declared.

4. The method of claim 3, further comprising:
    checking a shipping state storage location to determine whether the implantable device is in a shipping state or is instead in an implanted state; and
    establishing a value of the current threshold based on whether the implantable device is in the shipping state or is instead in the implanted state.

5. The method of claim 2, in which the measuring the current delivered by the battery includes averaging the measured current.

6. The method of claim 5, in which the averaging the measured current includes averaging over a second time period of about one day.

7. The method of claim 5, further comprising:
    comparing, to a current threshold, the average measured current delivered by the battery;
    declaring a current fault if the average measured current delivered by the battery exceeds the current threshold; and
    communicating to the user an indication of whether the current fault has been declared.

8. The method of claim 7, further comprising:
    checking a shipping state storage location to determine whether the implantable device is in a shipping state or is instead in an implanted state; and
    establishing a value of the current threshold based on whether the implantable device is in the shipping state or is instead in the implanted state.

9. The method of claim 5, in which the averaging the measured current includes averaging over a second time period of about one week.

10. The method of claim 5, further comprising:
    comparing, to a current threshold, the average measured current delivered by the battery; and
    establishing a value of the first voltage threshold using a result of the comparison of the average measured current delivered by the battery.

11. The method of claim 1, further comprising:
    measuring a temperature of the implantable medical device;
    comparing the measured temperature to a temperature threshold; and
    discounting the measured battery voltage if the measured temperature is below the temperature threshold.

12. The method of claim 1, further comprising:
    detecting whether the battery terminal voltage has fallen below a second voltage threshold, wherein the second voltage threshold is lower than the first voltage threshold, and wherein the second voltage threshold is a function of the measured rate at which the charge is delivered by the battery;
    communicating to the user an indication of whether the battery terminal voltage has fallen below the second voltage threshold; and
    altering functionality of the implantable medical device if the battery terminal voltage has fallen below the second voltage threshold.

13. A computer-readable medium including computer-executable instructions for performing a method comprising:
    measuring a battery terminal voltage of a battery of an implantable medical device;
    measuring a charge delivered by the battery during a first time period after the device has been implanted and before the battery terminal voltage falls below a first voltage threshold, wherein the first voltage threshold is a function of a measured rate at which the charge is delivered by the battery;
    calculating an available or depleted battery charge using the measured charge delivered by the battery during the first time period;
    communicating to a user an indication of the available or depleted battery charge; and
    communicating to the user an indication of whether the battery terminal voltage has fallen below the first voltage threshold.

14. A system comprising:
    an implantable medical device, the implantable medical device comprising:
        a battery;
        a battery terminal voltage measurement circuit, coupled to the battery, to measure a battery terminal voltage;
        a battery charge delivery measurement circuit, coupled to the battery, to monitor a charge delivered by the battery;
        a controller circuit, coupled to the battery terminal voltage measurement circuit to receive information about the measured battery terminal voltage, the controller circuit also coupled to the battery charge delivery measurement circuit to receive information about a rate at which charge is delivered from the battery, the controller circuit operative to compare the measured battery terminal voltage to a first voltage threshold, the controller circuit operative to compute the first voltage threshold using the information about the measured rate at which charge is delivered from the battery, the controller circuit operative to calculate an available or depleted battery charge using the measured charge delivered by the battery during a first time period after the device has been implanted and before the battery terminal voltage falls below the first voltage threshold; and a communication circuit, coupled to the controller, to communicate from the implantable device an indication of the available or depleted battery charge and an indication of whether the battery terminal voltage has fallen below the first voltage threshold.

15. The system of claim 14, in which the battery charge delivery measurement circuit includes a battery current measurement circuit to provide an indication of the battery current to the controller.

16. The system of claim 15, in which the controller includes a first memory storage location to store a current threshold, and the controller is operative to declare a current fault if the battery current exceeds the current threshold, and the communication circuit is operative to communicate an indication of the current fault from the implantable device.

17. The system of claim 16, further in which the controller includes a second memory storage location to store shipping state information indicative of whether the implantable device is in a shipping state, and in which the controller is operative to establish a value of the current threshold stored in the first memory storage location using whether the implantable device is in the shipping state.

18. The system of claim 15, in which at least one of the battery current measurement circuit and the controller includes an averaging circuit to average the measured current over an averaging time period.

19. The system of claim 14, in which the device further comprises:
a temperature sensor to measure a temperature of the implantable medical device;
wherein the controller is coupled to the temperature sensor to receive the measured temperature, and in which the controller includes a third memory storage location to store a temperature threshold, and in which the controller is operative to compare the measured temperature to the temperature threshold and to discount the battery voltage measurement if the temperature is below he temperature threshold.

20. The system of claim 14, further comprising:
a user interface, including a user interface communication circuit to communicate with the communication circuit of the implantable device, the user interface further including a display, the display including a displayed meter indicative of battery charge status of the battery in the implantable device, the display further including an indication of whether the measured battery voltage is below the first voltage threshold.

21. The system of claim 14, in which the controller includes a fourth memory storage location to store a second voltage threshold that is lower than the first voltage threshold, and wherein the controller circuit is operative to compare the measured battery terminal voltage to the second voltage threshold, and the controller circuit is operative to compute the second voltage threshold using the information about the measured rate at which charge is delivered from the battery, and the controller circuit is operative to alter functionality of the implantable device if the measured battery terminal voltage falls below the second voltage threshold, and in which the communication circuit is operative to communicate from the implantable device an indication of whether the battery terminal voltage has fallen below the second voltage threshold.

22. A system comprising:
an implantable medical device, the implantable medical device comprising:
a battery;
a battery terminal voltage measurement circuit, coupled to the battery, to measure a battery terminal voltage;
a battery charge delivery measurement circuit, coupled to the battery, to monitor a charge delivered by the battery;
means, coupled to the battery terminal voltage measurement circuit and the battery charge delivery measurement circuit, for comparing the measured battery terminal voltage to a first voltage threshold, wherein the first voltage threshold is a function of a measured rate at which the charge is delivered by the battery;
means, coupled to the battery charge delivery measurement circuit, for calculating an available or depleted battery charge using the measured charge delivered by the battery during a first time period after the device has been implanted and before the battery terminal voltage falls below the first voltage threshold; and
a communication circuit, coupled to the controller, to communicate from the implantable device an indication of the available or depleted battery charge and an indication of whether the battery terminal voltage has fallen below the first voltage threshold.

23. A method comprising:
measuring a battery terminal voltage of a battery of an implantable medical device;
measuring a charge delivered by the battery during a first time period after the device has been implanted and before the battery terminal voltage falls below a first voltage threshold, wherein measuring the charge delivered by the battery comprises measuring a current delivered by the battery, and wherein the first voltage threshold is a function of a measured rate at which the charge is delivered by the battery;
calculating an available or depleted battery charge using the measured charge delivered by the battery during the first time period;
communicating to a user an indication of the available or depleted battery charge;
communicating to the user an indication of whether the battery terminal voltage has fallen below the first voltage threshold;
checking a shipping state storage location to determine whether the implantable device is in a shipping state or is instead in an implanted state;
establishing a value of the current threshold based on whether the implantable device is in the shipping state or is instead in the implanted state;
comparing the measured current delivered by the battery to a current threshold;
declaring a current fault if the measured current delivered by the battery exceeds the current threshold; and
communicating to the user an indication of whether the current fault has been declared.

24. A method comprising:
measuring a battery terminal voltage of a battery of an implantable medical device;
measuring a charge delivered by the battery during a first time period after the device has been implanted and before the battery terminal voltage falls below a first voltage threshold, wherein measuring the charge delivered by the battery comprises measuring a current delivered by the battery, wherein measuring the current delivered by the battery includes averaging the measured current, and wherein the first voltage threshold is a function of a measured rate at which the charge is delivered by the battery;

calculating an available or depleted battery charge using the measured charge delivered by the battery during the first time period;

communicating to a user an indication of the available or depleted battery charge;

communicating to the user an indication of whether the battery terminal voltage has fallen below the first voltage threshold;

checking a shipping state storage location to determine whether the implantable device is in a shipping state or is instead in an implanted state;

establishing a value of the current threshold based on whether the implantable device is in the shipping state or is instead in the implanted state;

comparing, to a current threshold, the average measured current delivered by the battery;

declaring a current fault if the average measured current delivered by the battery exceeds the current threshold; and communicating to the user an indication of whether the current fault has been declared.

25. A method comprising:

measuring a battery terminal voltage of a battery of an implantable medical device;

measuring a charge delivered by the battery during a first time period after the device has been implanted and before the battery terminal voltage falls below a first voltage threshold, wherein measuring the charge delivered by the battery comprises measuring a current delivered by the battery, wherein measuring the current delivered by the battery includes averaging the measured current, and wherein the first voltage threshold is a function of a measured rate at which the charge is delivered by the battery;

comparing, to a current threshold, the average measured current delivered by the battery; and establishing a value of the first voltage threshold using a result of the comparison of the average measured current delivered by the battery.

calculating an available or depleted battery charge using the measured charge delivered by the battery during the first time period;

communicating to a user an indication of the available or depleted battery charge; and communicating to the user an indication of whether the battery terminal voltage has fallen below the first voltage threshold.

26. A system comprising:

an implantable medical device, the implantable medical device comprising:

a battery;

a battery terminal voltage measurement circuit, coupled to the battery, to measure a battery terminal voltage;

a battery charge delivery measurement circuit, coupled to the battery, to monitor a charge delivered by the battery, the battery charge delivery measurement circuit including a battery current measurement circuit to provide an indication of the battery current to the controller;

a controller circuit, coupled to the battery terminal voltage measurement circuit to receive information about the measured battery terminal voltage, the controller circuit also coupled to the battery charge delivery measurement circuit to receive information about a rate at which charge is delivered from the battery, the controller circuit operative to compare the measured battery terminal voltage to a first voltage threshold, the controller circuit operative to compute the first voltage threshold using the information about the measured rate at which charge is delivered from the battery, the controller circuit operative to calculate an available or depleted battery charge using the measured charge delivered by the battery during a first time period after the device has been implanted and before the battery terminal voltage falls below the first voltage threshold, the controller circuit including a first memory storage location to store a current threshold, the controller circuit operative to declare a current fault if the battery current exceeds the current threshold, the controller circuit including a second memory storage location to store shipping state information indicative of whether the implantable device is in a shipping state, the controller circuit operative to establish a value of the current threshold stored in the first memory storage location using whether the implantable device is in the shipping state; and a communication circuit, coupled to the controller, to communicate from the implantable device an indication of the available or depleted battery charge, an indication of whether the battery terminal voltage has fallen below the first voltage threshold, and an indication of the current fault from the implantable device.

27. A method comprising:

measuring a battery terminal voltage of a battery of an implantable medical device;

measuring a charge delivered by the battery during a first time period after the device has been implanted and before the battery terminal voltage falls below a first voltage threshold, wherein the first voltage threshold is a function of a measured rate at which the charge is delivered by the battery;

calculating an available or depleted battery charge using the measured charge delivered by the battery during the first time period;

communicating to a user an indication of the available or depleted battery charge; and providing a battery terminal voltage indication of battery status during a second time period after the battery terminal voltage has fallen below the first voltage threshold.

28. The method of claim 27, in which the measuring the charge delivered by the battery comprises measuring a current delivered by the battery.

29. The method of claim 28, farther comprising:

comparing the measured current delivered by the battery to a current threshold;

declaring a current fault if the measured current delivered by the battery exceeds the current threshold; and communicating to the user an indication of whether the current fault has been declared.

30. The method of claim 29, further comprising:

checking a shipping state storage location to determine whether the implantable device is in a shipping state or is instead in an implanted state; and establishing a value of the current threshold based on whether the implantable device is in the shipping state or is instead in the implanted state.

31. The method of claim 28, in which the measuring the current delivered by the battery includes averaging the measured current.

32. The method of claim 31, further comprising:
comparing, to a current threshold, the average measured current delivered by the battery;
declaring a current fault if the average measured current delivered by the battery exceeds the current threshold; and
communicating to the user an indication of whether the current fault has been declared.

33. The method of claim 32, further comprising:
checking a shipping state storage location to determine whether the implantable device is in a shipping state or is instead in an implanted state; and
establishing a value of the current threshold based on whether the implantable device is in the shipping state or is instead in the implanted state.

34. The method of claim 31, further comprising:
comparing, to a current threshold, the average measured current delivered by the battery; and
establishing a value of the first voltage threshold using a result of the comparison of the average measured current delivered by the battery.

35. The method of claim 27, further comprising:
measuring a temperature of the implantable medical device;
comparing the measured temperature to a temperature threshold; and
discounting the measured battery voltage if the measured temperature is below the temperature threshold.

36. The method of claim 27, further comprising:
detecting whether the battery terminal voltage has fallen below a second voltage threshold, wherein the second voltage threshold is lower than the first voltage threshold, and wherein the second voltage threshold is a function of the measured rate at which the charge is delivered by the battery;
communicating to the user an indication of whether the battery terminal voltage has fallen below the second voltage threshold; and
altering functionality of the implantable medical device if the battery terminal voltage has fallen below the second voltage threshold.

37. A system comprising:
an implantable medical device, the implantable medical device comprising:
a battery;
a battery terminal voltage measurement circuit, coupled to the battery, to measure a battery terminal voltage;
a battery charge delivery measurement circuit, coupled to the battery, to monitor a charge delivered by the battery;
a controller circuit, coupled to the battery terminal voltage measurement circuit to receive information about the measured battery terminal voltage, the controller circuit also coupled to the battery charge delivery measurement circuit to receive information about a rate at which charge is delivered from the battery, the controller circuit operative to compare the measured battery terminal voltage to a first voltage threshold, the controller circuit operative to compute the first voltage threshold using the information about the measured rate at which charge is delivered from the battery, the controller circuit operative to calculate an available or depleted battery charge using the measured charge delivered by the battery during a first time period after the device has been implanted and before the battery terminal voltage falls below the first voltage threshold; and
a communication circuit, coupled to the controller, to communicate from the implantable device an indication of the available or depleted battery charge during the first time period, the communication circuit to communicate a battery terminal voltage indication of battery status during a second time period after the battery terminal voltage has fallen below the first voltage threshold.

38. The system of claim 37, in which the battery charge delivery measurement circuit includes a battery current measurement circuit to provide an indication of the battery current to the controller.

39. The system of claim 38, in which the controller includes a first memory storage location to store a current threshold, and the controller is operative to declare a current fault if the battery current exceeds the current threshold, and the communication circuit is operative to communicate an indication of the current fault from the implantable device.

40. The system of claim 39, further in which the controller includes a second memory storage location to store shipping state information indicative of whether the implantable device is in a shipping state, and in which the controller is operative to establish a value of the current threshold stored in the first memory storage location using whether the implantable device is in the shipping state.

41. The system of claim 38, in which at least one of the battery current measurement circuit and the controller includes an averaging circuit to average the measured current over an averaging time period.

42. The system of claim 37, in which the device further comprises:
a temperature sensor to measure a temperature of the implantable medical device;
wherein the controller is coupled to the temperature sensor to receive the measured temperature, and in which the controller includes a third memory storage location to store a temperature threshold, and in which the controller is operative to compare the measured temperature to the temperature threshold and to discount the battery voltage measurement if the temperature is below he temperature threshold.

43. The system of claim 37, further comprising:
a user interface, including a user interface communication circuit to communicate with the communication circuit of the implantable device, the user interface further including a display, the display including a displayed meter indicative of battery charge status of the battery in the implantable device, the display further including an indication of whether the measured battery voltage is below the first voltage threshold.

44. The system of claim 37, in which the controller includes a fourth memory storage location to store a second voltage threshold that is lower than the first voltage threshold, and wherein the controller circuit is operative to compare the measured battery terminal voltage to the second voltage threshold, and the controller circuit is operative to compute the second voltage threshold using the information about the measured rate at which charge is delivered from the battery, and the controller circuit is operative to alter functionality of the implantable device if the measured battery terminal voltage falls below the second voltage threshold, and in which the communication circuit is operative to communicate from the implantable device an indication of whether the battery terminal voltage has fallen below the second voltage threshold.

* * * * *

UNITED STATES PATENT AND TRADEMARK OFFICE
CERTIFICATE OF CORRECTION

PATENT NO. : 7,194,308 B2
APPLICATION NO. : 10/706856
DATED : March 20, 2007
INVENTOR(S) : Krig et al.

It is certified that error appears in the above-identified patent and that said Letters Patent is hereby corrected as shown below:

Column 3, line 41, before "locations" delete "location".

Column 9, line 43, in Claim 19, delete "he" and insert -- the --, therefor.

Column 11, line 40, in Claim 25, after "battery" delete "." and insert -- ; --, therefor.

Column 12, line 50, in Claim 29, delete "farther" and insert -- further --, therefor.

Column 14, line 41, in Claim 42, delete "he" and insert -- the --, therefor.

Signed and Sealed this

Twelfth Day of June, 2007

JON W. DUDAS
*Director of the United States Patent and Trademark Office*